United States Patent [19]

Chou et al.

[11] Patent Number: 5,821,357
[45] Date of Patent: Oct. 13, 1998

[54] STEREOSELECTIVE GLYCOSYLATION PROCESS FOR PREPARING 2'-DEOXY-2',2'-DIFLUOROPURINE AND TRIAZOLE NUCLEOSIDES

[75] Inventors: Ta-Sen Chou; Charles D. Jones, both of Indianapolis, Ind.

[73] Assignee: Eli Lilly and Company, Indianapolis, Ind.

[21] Appl. No.: 44,996

[22] Filed: Apr. 7, 1993

Related U.S. Application Data

[63] Continuation-in-part of Ser. No. 902,150, Jun. 22, 1992, abandoned.

[51] Int. Cl.$^6$ .......................... C07H 1/00; C07H 19/073; C07H 19/173
[52] U.S. Cl. .................. 536/55.3; 536/26.7; 536/28.4
[58] Field of Search .................... 514/45, 46; 536/26.12, 536/27.1, 27.11, 27.13, 27.14, 27.21, 27.3, 27.4, 28.4, 28.5, 28.53, 28.54, 55.3, 26.71, 26.7

[56] References Cited

U.S. PATENT DOCUMENTS

| | | | |
|---|---|---|---|
| 3,282,921 | 11/1966 | Verheyden et al. | 260/211 |
| 4,145,531 | 3/1979 | Eckstein et al. | 536/26 |
| 4,211,773 | 7/1980 | Lopez et al. | 424/180 |
| 4,526,988 | 7/1985 | Hertel | 549/313 |
| 4,625,020 | 11/1986 | Brundidge et al. | 536/18 |
| 4,751,221 | 6/1988 | Watanabe et al. | 514/46 |
| 4,808,614 | 2/1989 | Hertel | 514/45 |
| 4,965,374 | 10/1990 | Chou et al. | 549/313 |
| 5,306,837 | 4/1994 | Bisacchi et al. | 556/419 |
| 5,371,210 | 12/1994 | Chou | 536/27.11 |

FOREIGN PATENT DOCUMENTS

| | | | |
|---|---|---|---|
| 145978 | 6/1985 | European Pat. Off. | C07H 13/00 |
| 211354 | 2/1987 | European Pat. Off. | C07H 19/073 |
| 219829 | 4/1987 | European Pat. Off. | C07H 19/16 |
| 339161 | 11/1989 | European Pat. Off. | C07F 9/65 |
| 345751 | 12/1989 | European Pat. Off. | A61K 31/70 |
| 0428109 | 5/1991 | European Pat. Off. | |
| 428109 | 5/1991 | European Pat. Off. | C07H 19/16 |
| 2125401 | 3/1984 | United Kingdom | C07D 4/05 |

OTHER PUBLICATIONS

Kennedy (Ed.) Carbohydrate Chemistry, Clarendon Press, Oxford, 1988, p. 154.
M. Robbins et al. JACS, vol. 98, #25 (8 Dec. '76) pp. 8204–8213.
J. March, "Advanced Organic Chemistry", McGraw–Hill Book Co., 1977, NY, pp. 325–327.
Z. Kazimierczuk et al. J. Am. Chem. Soc., vol. 106 (1984) pp. 6379–6382.
T.–L. Su et al. J. Org. Chem., vol. 46 (1981) pp. 1790–1792.
H.G. Howell et al. J. Org. Chem., vol. 53 (1988) pp. 85–88.
V.E. Marquez et al. Biochem. Pharmacology, vol. 36, #17 (1987) pp. 2719–2722.
M. Rasmussen et al. J. Am. Chem. Soc., vol. 89, #21 (1967) pp. 5439–5445.
R. P. Hodge, et al., *J. Org. Chem.*, 56, 1553–64 (1991).
*Chem. Abstracts*, 56, 11692–93 (1992).
Hubbard, et al., *Nucleic Acids Res.*, 12(17), 6827–37 (1984).
Kazimierczuk, et al., *Nucleic Acids Res.*, 12(2), 1179–92 (1984).
Tann, et al., *J. Org. Chem.*, 50, 3644–47 (1985).
Howell, et al., *J. Org. Chem.*, 53, 85–88 (1988).
Hoffer, et al., *Chem. Ber.*, 93, 2777–2781 (1960).
Shimadate, et al., *Nippon Kagaku Zasshi*, 82, 1268–70 (1961).
Shamadate, et al., *Nippon Kagaku Zasshi*, 81, 1440–41 (1960).

*Primary Examiner*—Gary L. Kunz
*Attorney, Agent, or Firm*—Brian P. Barrett; David E. Boone

[57] ABSTRACT

A stereoselective glycosylation process for preparing beta-anomer enriched 2'-deoxy-2',2'-difluoropurine and triazole nucleosides and 2'-deoxy-2'-fluoropurine and triazole nucleosides which involves reacting an alpha-anomer enriched 2-deoxy-2,2-difluorocarbohydrate or 2-deoxy-2-fluorocarbohydrate with at least a molar equivalent of a nucleobase derivative in a low freezing inert solvent.

9 Claims, No Drawings

STEREOSELECTIVE GLYCOSYLATION PROCESS FOR PREPARING 2'-DEOXY-2',2'-DIFLUOROPURINE AND TRIAZOLE NUCLEOSIDES

CROSS REFERENCE TO RELATED APPLICATIONS

This application is a continuation-in-part of Ser. No. 07/902,150, filed Jun. 22, 1992 now abandoned.

BACKGROUND OF THE INVENTION

1. Field of the Invention

The invention pertains to the field of pharmaceutical chemistry and provides a stereoselective glycosylation process for preparing 2'-deoxy-2',2'-difluoropurine and triazole nucleosides and 2'-deoxy-2'-fluoropurine and triazole nucleosides.

2. State of the Art

The continued interest in the synthesis of 2'-deoxynucleosides and their analogues is reflected in their successful use as therapeutic agents in viral and cancerous diseases. A critical step in the synthesis of 2'-deoxynucleosides is the condensation of the nucleobase and carbohydrate to form the N-glycosidic bond. When the carbohydrate possesses a 2-hydroxy substituent, the substituent provides a substantial degree of 1,2-anchiomeric assistance, which facilitates stereoselective glycosylation. However, processes for synthesizing of 2'-deoxynucleosides are typically non-stereoselective and form a mixture of alpha and beta nucleosides.

Another type of condensation is fusion glycosylation, which is carried out in the absence of a solvent and at reaction temperatures sufficient to convert the carbohydrate and nucleoside base reactants to a molten phase. The original fusion glycosylation process was used to prepare purine nucleosides and involved reacting a peracylated sugar with a fusible purine base under vacuum and in the presence of a catalyst, such as p-toluenesulfonic acid. However, the glycosylation was not effective in condensing pyrimidine nucleosides because of their high melting points. In addition, the yields would vary widely and a broad range of anomerically mixed nucleoside products were produced.

T. Shimadate, et al., in *Nippon Kagaku Zasshi*, 81, 1440–1444 (1960) and *Chem. Abstracts*, 56, 11692 (1962), described a fusion glycosylation process involving reacting a peracetylated arabinofuranose and a purine base in the molten phase, under vacuum, in the presence of a p-toluenesulfonic acid catalyst. T. Shimadate, *Nippon Kagaku Zasshi*, 82, 1268–1270 (1961), described a similar fusion glycosylation process using an anhydrous zinc dichloride catalyst.

R. P. Hodge, et al., *J. Org. Chem.*, 56, 1553–1564 (1991), described the preparation of deoxythymidine, deoxycytidine, deoxyadenosine and deoxyguanosine nucleosides containing deuterium at the C-1' position of the carbohydrate 1-chloro-3,5-ditoluoylribofuranose. The glycosylation was based on the synthesis described in Hubbard, et al., *Nucleic Acids Res.*, 12, 6827 (1984). The preparation of 2'-deoxycytidine required converting a silylated uridine derivative to a silylated cytidine derivative by one of the three different methods. In each, substantial quantities of undesirable alpha-anomer nucleoside product formed. Also, isolating the small quantity of beta-anomer nucleoside obtained from the anomeric mixture proved to be difficult.

The synthesis of purine deoxynucleosides was carried out by the procedure described in Robbins, *Nucleic Acids Res.*, 12, 1179 (1984), and involved a reacting a sodium salt of a halopurine with 1-chloro-3,5-ditoluoylribofuranose. The sodium salts of purine bases were found to be much better nucleophiles than silylated pyrimidine bases.

U.S. Pat. No. 4,526,988, Hertel, illustrated a fusion glycosylation process for preparing 2'-deoxy-2',2'-difluoronucleosides which involves reacting a 3,5-bis(t-butyldimethylsilyloxy)-1-methanesulfonyloxy-2-deoxy-2,2-difluororibofuranose with 5-methyl-2,4-bis(trimethylsilyloxy)-pyrimidine at 150° C.

Some deoxynucleosides have been prepared in high yield from deoxyhalogenose with Friedel-Crafts catalysts, notably, 1-chloro-2-deoxy-3,5-di-p-toluoyl-alpha-D-erythropentofuranose; see, M. Hofer, *Chem. Ber*, 93, 2777 (1960). However, halogenoses are less stable thermally than peracylated carbohydrates and produce a 1:1 alpha to beta-anomeric mixture of nucleoside products. Walker, et al., *Nucleic Acid Research*, 12, 6827 (1984), used halogenose in condensation reactions to study the factors controlling the anomeric ratio of nucleoside products and found that beta-anomer nucleosides were formed exclusively from alpha-halocarbohydrates via $S_N2$ displacement. The corresponding alpha-anomer nucleoside contamination was determined to result from the anomerization of alpha-halo carbohydrate to beta-halo carbohydrate before the $S_N2$ displacement reaction occurs. Walker, et al., found that by changing the solvent or catalyst higher yields of the desired beta-anomer nucleoside were produced.

R. P. Hodge et. al., *J. Org. Chem.*, 56, 1553 (1991), described preparing pyrimidine and purine nucleosides containing deuterium at the C-1' position by the method described by Walker, et al. 1'-Deuterium-2'-deoxycytidine was prepared by reacting a carbohydrate and silylated cytosine derivative but the reaction gave poor yields. However, the yield was significantly improved when silylated uridine derivatives were used.

The synthesis of 2'-deoxy-2'-fluoronucleosides advanced rapidly when a procedure for synthesizing 2-deoxy-2-fluoro-3,5-di-O-benzoyl-alpha-D-arabinosyl bromide was made available; see Tann, et. al., *J. Org. Chem.*, 50, 3644 (1985) and Howell, et. al., *J. Org. Chem.*, 53, 85 (1988). It was discovered that 2-deoxy-2-fluoro-3,5-di-O-benzoyl-alpha-D-arabinosyl bromide did not anomerize in dry acetonitrile over extended periods. Therefore, high yields of beta-nucleosides could be obtained from 2-deoxy-2-fluoro-3,5-di-O-benzoyl-alpha-O-arabinosyl bromide via $S_N2$ displacement. Also, stereoselectivity of the nucleoside products could be achieved if either carbon tetrachloride or chloroform solvents was employed.

The formation of the N-glycoside bond in 2'-deoxy-2',2'-difluoronucleoside synthesis is much more difficult than in instances where the carbohydrate is 1,2-anchiometric assisted or contains only 1 fluorine at the C-2 position. The traditional carbohydrate leaving groups, such as acetate, chloride and bromide, render the carbohydrate inactive. In order to overcome this problem, Hertel, U.S. Pat. No. 4,526,988, relied on more reactive sulfonate leaving groups being attached to the carbohydrate to affect its reactivity. For example, hydroxy protected carbohydrates, such as 2-deoxy-2,2-difluoro-D-ribofuranose, containing methanesulfonate, toluenesulfonate, ethanesulfonate, isopropanesulfonate or 4-methoxybenzenesulfonate as a leaving group at the C-1 position, were reacted with a protected nucleobase at temperatures of 50° C. to 220° C., in the presence of a high boiling solvent, such as dimethylformamide, dimethylacetamide and hexamethylphosphoramide. Hertel teaches that when carrying out the glycosylation reaction at elevated pressures, any convenient inert solvent, such as ethers, halogenated alkanes, and aromatics, can be used since the elevated pressure eliminates the loss of low boiling inert solvents due to evaporation. However, at reaction temperatures from room temperature to 100° C., a catalyst such as trifluoromethanesulfonyloxysilane is required.

U.S. Pat. No. 4,965,374, Chou, et al., reports that Hertel's condensation method provides alpha-anomer stereoselectively in a 4:1 alpha to beta anomeric ratio of nucleoside products and goes on to describe an improved procedure, based on the Vorbruggen condensation method, that employs a pivotol intermediate of 2-deoxy-2,2-difluoro-3,5-di-O-benzoyl-alpha-D-arabinosyl methanesulfonate. However, Chou's condensation method forms a 1:1 alpha to beta anomer mixture of nucleoside products.

Despite the preceding advances in nucleoside synthesis, there continues to be a need for a stereoselective glycosylation process capable of efficiently producing beta-anomer enriched 2'-deoxy-2',2'-difluoropurine nucleosides and 2'-deoxy-2'-fluoropurine nucleosides in high yield and in the absence of a catalyst for reactive and relatively unreactive nucleobase derivatives.

Accordingly, one object of the present invention is to provide a stereoselective glycosylation process for preparing beta-anomer enriched 2'-deoxy-2',2'-difluoropurine and triazole nucleosides and 2'-deoxy-2'-fluoropurine and triazole nucleosides at reaction temperatures below 50° C.

Another object of the present invention is to provide a stereoselective glycosylation process for preparing beta-anomer enriched 2'-deoxy-2',2'-difluoropurine and triazole nucleosides and 2'-deoxy-2'-fluoropurine and triazole nucleosides without the use of a catalyst.

Another object of the present invention is to provide a stereoselective glycosylation process for preparing beta-anomer enriched 2'-deoxy-2',2'-difluoropurine and triazole nucleosides and 2'-deoxy-2'-fluoropurine and triazole nucleosides capable of employing reactive and relatively unreactive nucleobase derivatives.

Another object of the present invention is to provide a stereoselective glycosylation process for preparing beta-anomer enriched 2'-deoxy-2',2'-difluoropurine and triazole nucleosides and 2'-deoxy-2'-fluoropurine and triazole nucleosides in yields higher than those produced by conventional glycosylation procedures.

Yet another object of the present invention is to provide a stereoselective glycosylation process for preparing beta-anomer enriched 2'-deoxy-2',2'-difluoropurine and triazole nucleosides and 2'-deoxy-2'-fluoropurine and triazole nucleosides offering a means for isolating beta-anomer enriched nucleosides in the form of a crude product or acid addition salt, such as a hydrochloride salt.

Other objects and advantages of the present invention will become apparent from the following description of embodiments.

SUMMARY OF THE INVENTION

The invention is a stereoselective glycosylation process for preparing a beta-anomer enriched nucleoside of the formula

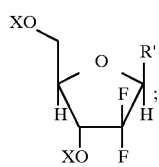

wherein each X is independently selected from hydroxy protecting groups and R' is a nucleobase selected from the group consisting of

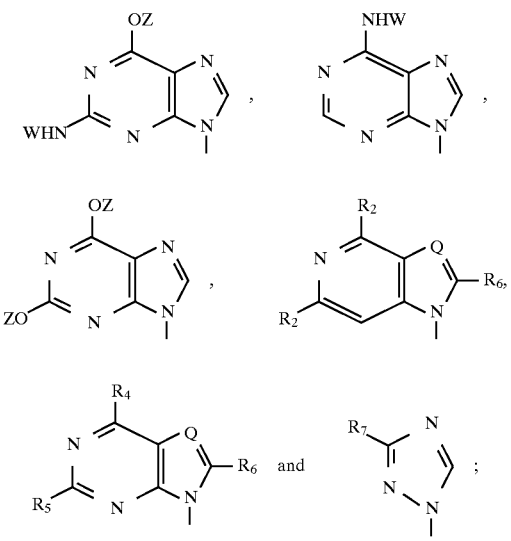

wherein $R_2$ is cyano, azido or halo; $R_4$, $R_5$ and $R_6$ are independently selected from the group consisting of hydrogen, —OZ, —NHW, N(alkyl)W, halo, alkoxy, azido, cyano and thioalkyl; $R_7$ is selected from the group consisting of hydrogen, halo, cyano, alkyl, alkoxy, alkoxycarbonyl, thioalkyl, thiocarboxamido and carboxamido; Q is selected from the group consisting of CH, $CR_8$ and N; wherein $R_8$ is selected from the group consisting of halo, carboxamido, thiocarboxamido, alkoxycarbonyl and cyano; Z is a hydroxy protecting group and W is an amino protecting group; comprising reacting an alpha-anomer enriched 2,2-difluorocarbohydrate of the formula

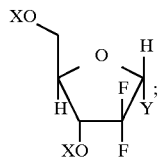

wherein Y is selected from the group consisting of trifluoromethanesulfonyloxy, 1,1,1-trifluoroethanesulfonyloxy, octafluorobutanesulfonyloxy and nonafluorobutanesulfonyloxy and X is as defined above; with at least a molar equivalent of a nucleobase derivative, R", selected from the group consisting of

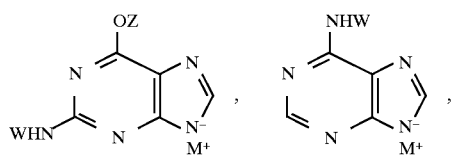

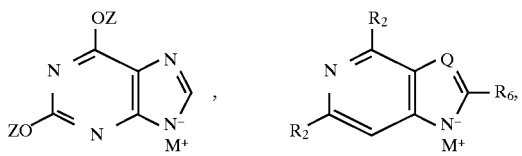
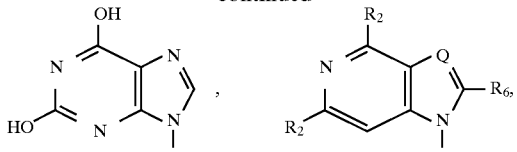

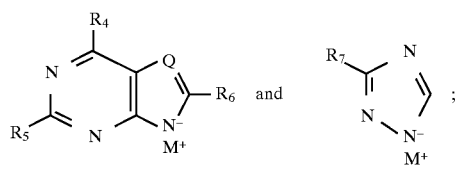 and 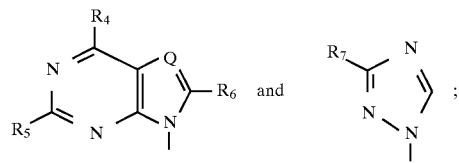 and wherein $R_2$ through $R_7$, Q, Z and W are as defined above and $M^+$ is a metal cation; in a low freezing inert solvent.

In another aspect, the invention is a stereoselective glycosylation process for preparing a beta-anomer enriched nucleoside of the formula

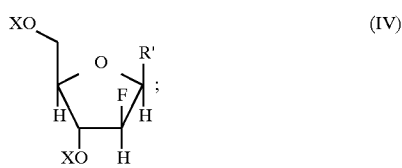 (IV)

wherein X and R' are as defined above; comprising reacting an alpha-anomer enriched 2-fluorocarbohydrate of the formula

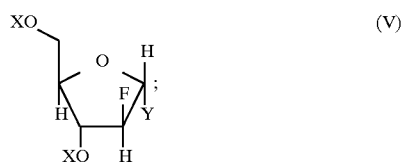 (V)

wherein Y and X are as defined above; with at least a molar equivalent of a nucleobase derivative, R"; wherein R" is as defined above; in a low freezing inert solvent.

The invention also provides a stereoselective glycosylation process for preparing a beta-anomer enriched nucleoside of the formula

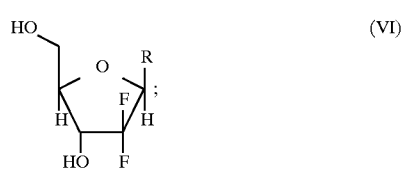 (VI)

wherein R is a deblocked nucleobase selected from the group consisting of

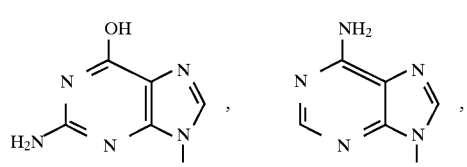

wherein $R_2$ is halo; $R_4$, $R_5$ and $R_6$ are independently selected from the group consisting of hydrogen, —OH, —NH$_2$, N(alkyl), halo, alkoxy and thioalkyl; $R_7$ is selected from the group consisting of hydrogen, halo, cyano, alkyl, alkoxy, alkoxycarbonyl, thioalkyl, thiocarboxamide and carboxamide; Q is selected from the group consisting of CH, CR$_8$ and N; wherein R$_8$ is selected from the group consisting of halo, carboximide, thiocarboximide, alkoxycarbonyl and nitrile; comprising reacting an alpha-anomer enriched 2,2-difluorocarbohydrate of the formula

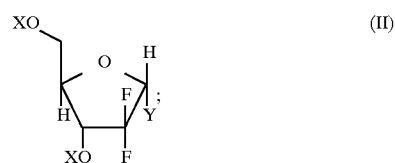 (II)

wherein Y and X are as defined above; with at least a molar equivalent of a nucleobase derivative, R"; wherein R" is as defined above; in a low freezing inert solvent; and deblocking.

Also provided is a stereoselective glycosylation process for preparing a beta-anomer enriched nucleoside of the formula

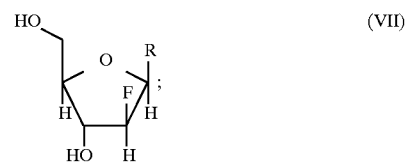 (VII)

wherein R is a deblocked nucleobase as defined above; comprising reacting an alpha-anomer enriched 2-fluorocarbohydrate of the formula

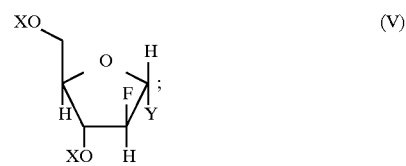 (V)

wherein Y and X are as defined above; with at least a molar equivalent of a nucleobase derivative, R"; wherein R" is as defined above; in a low freezing inert solvent; and deblocking.

DETAILED DESCRIPTION OF THE INVENTION

Throughout this document, all temperatures are in degrees Celsius, all proportions, percentages and the like, are in weight units and all mixtures are in volume units, except where otherwise indicated. Anomeric mixtures are expressed as a weight/weight ratio or as a percent. The term "xylenes" alone or in combination refers to all isomers of xylene and mixtures thereof. The term "lactol" alone or in combination refers to a 2-deoxy-2,2-difluoro-D-ribofuranose or 2-deoxy-2-fluoro-D-ribofuranose. The term "carbohydrate" alone or in combination refers to an activated lactol wherein the hydroxy group at the C-1 position has been replaced by a desirable leaving group. The term "halo" alone or in combination refers to chloro, iodo, fluoro and bromo. The term "alkyl" alone or in combination refers to straight, cyclic and branched chain aliphatic hydrocarbon groups which preferably contain up to 7 carbon atoms, such as methyl, ethyl, n-propyl, isopropyl, n-butyl, t-butyl, n-pentyl, n-hexyl, 3-methylpentyl groups and the like or substituted straight, cyclic and branched chain aliphatic hydrocarbons, such as chloroethyl, 1,2-dichloroethyl, and the like. The term "alkoxy" alone or in combination refers to the general formula AO; wherein A is alkyl. The term "aryl" alone or in combination refers to carbocyclic or heterocyclic groups such as phenyl, naphthyl, thienyl and substituted derivatives thereof. The term "thioalkyl" alone or in combination refers to the general formula BS; wherein B is alkyl or hydrogen. The term "ester" alone or in combination refers to the general formula EOOC; wherein E is alkyl or aryl. The term "aromatic" alone or in combination refers to benzene like structures containing (4n+2) delocalized π electrons. The terms "sulfonate" or "sulfonyloxy" alone or in combination refer to the general formula $GSO_3$; wherein G is alkyl or aryl. The term "substituted" alone or in combination refers to substitution by at least one or more of the groups selected from cyano, halo, carboalkoxy, toluoyl, nitro, alkoxy and dialkylamino. The phrase "anomer enriched" alone or in combination refers to an anomeric mixture wherein the ratio of a specified beta- or alpha-anomer is greater than 1:1 and includes a substantially pure anomer.

In accordance with the present glycosylation process, beta-anomer enriched 2'-deoxy-2',2'-difluoronucleosides and 2'-deoxy-2'-fluoronucleosides are prepared by reacting an alpha-anomer enriched carbohydrate of formulas II and V with at least a molar equivalent of a protected nucleobase derivative in a low freezing inert solvent as shown in the following reaction schemes:

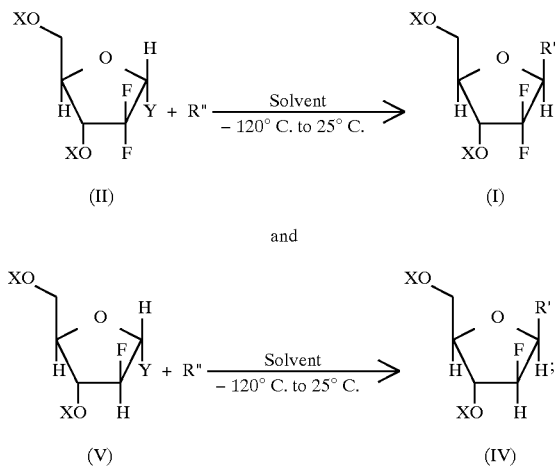

wherein X, Y, R" and R' are as defined above. While not wishing to be bound by theory, it is believed that the glycosylation reaction proceeds primarily via $S_N2$ displacement. Therefore, the beta-anomer enriched nucleoside products are predominantly derived from alpha-anomer enriched carbohydrates.

The lactol starting materials suitable for use in the present glycosylation process are commonly known in the art and can be readily synthesized by standard procedures commonly employed by those of ordinary skill in the art. For example, U.S. Pat. No. 4,526,988 teaches the synthesis of 2-deoxy-2,2-difluoro-D-ribofuranoses of formula III and Reichman, et al., *Carbohydr. Res.,* 42, 233 (1975) teaches the synthesis of 2-deoxy-2-fluoro-D-ribofuranoses of the formula VI. In a preferred embodiment, 2-deoxy-2,2-difluoro-D-ribofuranose-3,5-dibenzoate of formula III is used to prepare the blocked nucleoside products under the present invention.

Glycosylation reactions typically require protecting the oxygen atoms of the hydroxy groups of the lactol of formulas III and VI to prevent the hydroxy groups from reacting with the nucleobase derivative, or being decomposed in some manner. Hydroxy protecting groups (X) suitable for use in the present glycosylation process may be chosen from known protecting groups used in synthetic organic chemistry. Each hydroxy protecting group selected is preferably capable of being efficiently placed on the lactol and easily removed therefrom once the glycosylation reaction is complete. Hydroxy protecting groups known in the art are described in Chapter 3 of *Protective Groups in Organic Chemistry,* McOmie Ed., Plenum Press, New York (1973) and Chapter 2 of *Protective Groups in Organic Synthesis,* Green, John, J. Wiley and Sons, New York (1981); preferred are ester forming groups such as formyl, acetyl, substituted acetyl, propionyl, butaynoyl, pivaloyl, 2-chloroacetyl, benzoyl, substituted benzoyl, phenoxycarbonyl, methoxyacetyl; carbonate derivatives such as phenoxycarbonyl, ethoxycarbonyl, t-butoxycarbonyl, vinyloxycarbonyl, 2,2,2-trichloroethoxycarbonyl and benzyloxycarbonyl; alkyl ether forming groups such as benzyl, diphenylmethyl, triphenylmethyl, t-butyl, methoxymethyl, tetrahydropyranyl, allyl, tetrahydrothienyl, 2-methoxyethoxy methyl; and silyl ether forming groups such as trialkylsilyl, trimethylsilyl, isopropyldialkylsilyl, alkyldiisopropylsilyl, triisopropylsilyl, t-butyldialkylsilyl and 1,1,3,3-tetraisopropyldisloxanyl; carbamates such as N-phenylcarbamate and N-imidazoylcarbamate; however more preferred are benzoyl, mono-substituted benzoyl and disubstituted benzoyl, acetyl, pivalamido, triphenylmethyl ethers, and silyl ether forming groups, especially t-butyldimethylsilyl; while most preferred is benzoyl.

In attaching each hydroxy protecting group to the lactol typical reactions conditions are employed and depend on the nature of the protecting group chosen. Typical reaction conditions are described in U.S. Pat. No. 4,526,988, which is incorporated herein by reference.

To obtain an efficient reaction of the nucleobase derivative and carbohydrate, an appropriate leaving group is stereoselectively attached to the lactol of formulas III and VI which activates the lactol and generates the alpha-anomer enriched carbohydrate of formulas II and V. The leaving group (Y) of the carbohydrate may be selected from the group consisting of trifluoromethanesulfonyloxy, 1,1,1-trifluoroethanesulfonyloxy, octafluorobutanesulfonyloxy ($C_4F_8HSO_3$) and nonafluorobutanesulfonyloxy ($C_4F_9SO_3$); more preferred is trifluoromethanesulfonyloxy.

The alpha-anomer enriched carbohydrate of formulas II and V are prepared by reacting the lactol of formulas III and VI with an amine base such as triethylamine, trimethylamine, tributylamine, dibutylamine, diethylmethylamine, dimethylethylamine, benzylmethylamine, N-methylmorpholine, tripropylamine, dipropylethylamine, N,N-dimethylbenzylamine, diisopropylethylamine, diethylamine, 1,8-diazabicyclo [5.4.0]undec-7-ene and 1,5-diazabicyclo[4.3.0]non-5-ene. However, the use of secondary amine bases may interfere with subsequent sulfonation, therefore care must be taken to limit the reaction time and maintain low temperatures when secondary amine bases are employed. The amine base preferably has a pKa of from about 8 to about 20 and is employed in a range of from about 1 molar equivalent to about 2 molar equivalents and more preferably from about 1.2 molar equivalents to about 1.5 molar equivalents. The reaction is carried out in an inert solvent having a freezing point temperature preferably below −78° C. Preferred solvents are selected from the group consisting of dichloromethane, 1,2-dichloroethane, dichlorofluoromethane, acetone, toluene, anisole, chlorobenzene, and mixtures thereof. The temperature of the solvent mixture is adjusted preferably in the range from about −40° C. to about −120° C. and more preferably below about −78° C. While not wishing to be bound by theory it is believed that the low temperature shifts the alpha to beta anomeric ratio of the lactol in favor of the alpha-anomer in a range from about 2:1 to about 4:1 alpha to beta. For example, a compound of formula III, where X is benzoyl, was added to dichloromethane and triethylamine at room temperature for 30 minutes. Next, the temperature of the solvent mixture was lowered. An $^{19}F$ NMR, taken at the various temperatures, showed an increase in the alpha to beta ratio of the ionized lactol as the temperature was lowered:

| Temperature | Alpha/Beta Ratio |
|---|---|
| 19° C. | 2.0:1 |
| −3° C. | 2.3:1 |
| −23° C. | 2.5:1 |
| −43° C. | 3.0:1 |
| −63° C. | 3.6:1 |
| −83° C. | 4.4:1 |

The ionized lactol is then trapped in solution at the low temperature and higher alpha-anomer ratio by adding a sulfonating reagent which forms an alpha-anomer enriched carbohydrate.

The sulfonating reagents are selected from the group consisting of trifluoromethanesulfonic anhydride, 1,1,1-trifluoroethanesulfonic halide, 1,1,1-trifluoroethanesulfonic anhydride, octaflic acid halide, octaflic acid anhydride, nanoflic acid halide and nanoflic acid anhydride, depending on the leaving group desired; more preferred is trifluoromethanesulfonic anhydride. The alpha-anomer enriched carbohydrates prepared from the ionized lactol, especially carbohydrates containing trifluoromethanesulfonyloxy, are unstable at room temperature and therefore are preferably used in-situ. Also, due to the reactivity of the sulfonating reagents, the glycosylation reaction may be carried out in a batch or continuous mode for large scale operations.

The nucleobases (R") employed herein are commonly known to organic chemist and no discussion of their synthesis is necessary. However, in order to be useful in the present glycosylation process the nucleobase derivatives (R") or their tautomeric equivalents, bearing amino or hydroxy groups preferably contain primary amino protecting groups (W) and/or hydroxy protecting groups (Z), depending on the nature of the nucleobase derivative selected. The protecting group blocks the hydroxy or amino groups which may provide a competing reaction site for the alpha-anomer carbohydrate. The protecting groups are attached to the nucleobase derivative (R") before it is reacted with the alpha-anomer enriched carbohydrate of formulas II and V and are removed subsequent thereto. A procedure for protecting the nucleobase derivatives is described in U.S. Pat. No. 4,526,988, which is incorporated herein by reference.

Preferred amino protecting groups (W) for purine nucleobase derivatives are selected from the group consisting of alkylcarbonyls, haloalkylcarbonyls and arylcarbonyls such as pivaloyl, trifluoroacetyl, naphthoyl, formyl and acetyl. Other suitable amino protecting groups are 2-trialkylsilylethoxymethyl, 4-methoxybenzyl, 3,4-dimethoxybenzyl, t-butyl, phthalimido, tetrahydropyranyl, tetrahydrofuranyl, methoxymethyl ether, methoxythiomethyl, trityl, t-butyldimethylsilyl, t-hexyldimethylsilyl, triisopropylsilyl, trichloroethoxycarbonyl, and sulfonyls such as alkylsulfonyls and arylsulfonyls. The more preferred amino protecting group is pivaloyl. Besides serving as an amino protecting group, the pivaloyl protecting group increases the solubility of notoriously insoluble purine nucleobase derivatives and directs the N-glycosidic coupling of the purine bases to the 9 regioisomer as opposed to the 7 regioisomer. Preferred hydroxy protecting groups (Z) for purine nucleobase derivatives are selected from the group consisting of ether forming groups such as benzyl, t-butyl, trityl, tetrahydropyranyl, tetrahydrofuranyl, methoxymethyl; ester forming groups such as formyl, acetyl, propionyl, pivaloyl, benzoyl and substituted benzoyl; carbonates such as carbobenzoxy, t-butoxycarbonyl, carbethoxy, vinyloxycarbonyl; carbamates, such as N,N-dialkylcarbamoyl; trialkylsilyl ethers such as t-butyltrimethylsilyl, t-hexyldimethylsilyl, triisopropylsilyl; more preferred is pivaloyl.

In addition, it is often advisable to convert any keto oxygen atoms on the nucleobase derivative to protected enol form. This makes the nucleobase derivative more aromatic and enhances the reactivity of the nucleobase derivative with the alpha-anomer enriched carbohydrate of formulas II and V. It is most convenient to enolize the keto oxygens and provide silyl protecting groups for them.

The nucleobase derivatives (R") employed in the present process are converted to metal cation salts to enhance their nucleophilic reactivity with the alpha-anomer enriched carbohydrate of formulas II and V. Suitable cation salt derivatives are prepared by adding a base, selected from the group consisting of sodium t-butoxide, sodium hydride, sodium hydroxide, sodium methoxide, sodium ethoxide, sodium diisopropylamide, lithium hydride, potassium hydride, potassium hydroxide, potassium methoxide, potassium ethoxide and potassium t-butoxide, to the nucleobase derivative in a solvent. The solvent may be selected from the group consisting of acetonitrile, dimethylformamide, dimethylacetamide, 1,3-dimethyl-2-imidazolidinone, tetrahydrofuran, sulfolane, N-methylpyrrolidinone, dimethylsulfoxide and mixtures thereof. The solvent may be removed prior to the glycosylation reaction or admixed with the glycosylation reaction solvent, provided the admixture is substantially inert to the glycosylation reaction.

The reaction solvents suitable for use in the present glycosylation process must be inert to the glycosylation reaction and have a freezing point temperature from about 40° C. to about −120° C. Preferred reaction solvents are selected from the group consisting of dichloromethane, 1,2-dichloroethane, dichlorofluoromethane, acetone, toluene, anisole, chlorobenzene, methylcyano and mixtures thereof; more preferred is dichloromethane.

In accordance with the present process, at least an equimolar amount of nucleobase derivative (R") must be employed relative to the amount of carbohydrate employed. However, it is more preferable to use a molar excess of nucleobase derivative in amounts greater than 1 molar equivalent to about 20 molar equivalents, depending on the nature of the nucleobase derivative selected; preferred is from about 1 equivalent to about 10 equivalents and more preferred is from about 2 equivalents to about 4 equivalents.

Although not critical, it is advisable that the reaction between the alpha-anomer enriched carbohydrate of formulas II and V and the nucleobase derivative be carried out in a dry atmosphere, e.g. in dry air, nitrogen or argon since certain nucleobase derivatives are moisture sensitive.

As mentioned above, certain alpha-anomer carbohydrates of formulas II and V are unstable at room temperature. Therefore, the glycosylation reaction is carried out at or below room temperature and more preferably carried out from about 25° C. to about −120° C. However, the glycosylation reaction temperature employed will depend on the leaving group attached to the alpha-anomer carbohydrate. For example, when the leaving group (Y) is trifluoromethanesulfonate, the preferred reaction temperature ranges from about −50° C. to about 10° C. while about −20° C. to about 0° C. is most preferred. On the other hand, when the leaving group (Y) is 1,1,1-trifluoroethanesulfonate, octafluorobutanesulfonyloxy or nonafluorobutanesulfonyloxy, the preferred reaction temperature ranges from about −20° C. to about 25° C. while about 0° C. to about 10° C. is most preferred. The glycosylation reaction is preferably carried out under atmospheric pressure and is substantially complete in about 5 minutes to about 1 hour.

The progress of the the present glycosylation process may be followed by procedures well known to one of ordinary skill in the art such as high pressure liquid chromatography (HPLC) and thin layer chromatography (TLC) which can be used to detect the presence of nucleoside product.

In accordance with the present glycosylation process, the beta-anomer enriched nucleosides are prepared in an anomer ratio greater than 1:1 to about 1:7 alpha to beta.

The final phase of the reaction sequence is the removal of the protecting groups X, Z and/or W from the blocked nucleoside of formula I or IV. The same anomeric ratio of unprotected nucleoside is obtained by removal of the protecting groups.

Most silyl and silyl-amino protecting groups are easily cleaved by use of a protic solvent, such as water or an alcohol. The acyl protecting groups, such as benzoyl and the acyl-amino protecting groups, are removed by hydrolysis with a strong base at a temperature from about 0° C. to about 100° C. Strong or moderately strong bases suitable for use in this reaction are bases which have a pKa (at 25° C.) of about 8.5 to about 20.0. Such bases include alkali metal hydroxides such as sodium or potassium hydroxide; alkali metal alkoxides such as sodium methoxide or potassium t-butoxide; alkali metal amides; amines such as diethylamine, hydroxylamine, ammonia and the like; and other common bases such as hydrazine and the like. At least one equivalent of base is needed for each protecting group.

The acyl protecting groups can also be removed with acid catalysts, such as methanesulfonic acid, hydrochloric acid, hydrobromic acid, sulfuric acid, or with acidic ion exchange resins. It is preferred to carry out such hydrolysis at relatively high temperature, such as the reflux temperature of the mixture, but temperatures as low as ambient may be used when particularly strong acids are used.

The removal of ether protecting groups is carried out by known methods, for example, with ethanethiol and aluminum chloride.

The t-butyldimethylsilyl protecting group requires acid conditions, such as contact with gaseous hydrogen halide, for its removal.

Removal of the protecting groups may be conveniently carried out in alcoholic solvents, especially aqueous alkanols such as methanol. However, the deblocking reaction may also be carried out in any convenient solvent, such as polyols including ethylene glycol, ethers such as tetrahydrofuran, ketones such as acetone and methyl ethyl ketone, or dimethylsulfoxide.

In a preferred embodiment, the deblocking reaction employs ammonia to remove a benzoyl hydroxy-protecting group at a temperature of about 10° C. It is preferable, however, to use an excess of base in this reaction, although the amount of excess base used is not crucial.

The resulting beta-anomer enriched nucleosides of formula VI or VII may be extracted and/or isolated from the reaction mixture by the techniques described in U.S. Pat. No. 4,965,374, Chou, which is incorporated herein by reference.

The following examples illustrate specific aspects of the present invention and are not intended to limit the scope thereof in any respect and should not be so construed.

EXAMPLE 1

Preparation of beta-anomer enriched 9-[1-(2'-deoxy-2',2'-difluoro-3',5'-di-O-benzoyl-D-ribofuranosyl)]-2, 6-dipivalamidopurine with 2 equivalents of 2,6-dipivalamidopurine potassium salt To 100 mg of 2-deoxy-2,2-difluoro-D-ribofuranosyl-3,5-dibenzoate were added 1 ml of dichloromethane and 0.036 ml of triethylamine. This solution was stirred at 23° C. for 15 minutes, cooled to −40° C. and reacted with 0.045 ml of trifluoromethanesulfonic anhydride to form alpha-anomer enriched 2-deoxy-2,2-difluoro-D-ribofuranosyl-3,5-dibenzoyl-1-trifluoromethanesulfonate in solution.

A 185 mg suspension of 2,6-dipivalamidopurine was prepared in 1.5 ml of acetonitrile and maintained anhydrous under a nitrogen atmosphere. 65 mg of potassium t-butoxide were added to the suspension and the resulting mixture was stirred at 23° C. for 10 minutes to form a 2,6-dipivalamidopurine potassium salt. The salt was cooled, to 0° C. and reacted with the alpha-anomer enriched 2-deoxy-2,2-difluoro-D-ribofuranosyl-3,5-dibenzoyl-1-trifluoromethanesulfonate solution, stirred for 1 hour and warmed to 22° C. to form the titled blocked nucleoside which was confirmed by HPLC analysis. The beta to alpha anomeric ratio of the blocked nucleoside was 2:1.

To extract the nucleoside product from the reaction mixture, 25 ml of ethyl acetate, 1 ml of water, 1 ml of 1N hydrochloric acid and 2 ml of a saturated aqueous sodium chloride solution were added. The organic layer was separated, washed with 5 ml of saturated aqueous sodium bicarbonate solution, 5 ml of brine and dried over magnesium sulfate. A quantitative HPLC analysis revealed a combined yield of blocked beta- and alpha-anomer nucleoside of 42 percent.

EXAMPLE 2

Preparation of beta-anomer enriched 9-[1-(2'-deoxy-2',2'-difluoro-3',5'-di-O-benzoyl-D-ribofuranosyl)]-2, 6-dipivalamidopurine with 2 equivalents of 2,6-dipivalamidopurine potassium salt To 1 g of 2-deoxy-2,2-difluoro-D-ribofuranosyl-3,5-dibenzoate was added 0.55 ml of triethylamine and 8.33 ml of dichloromethane at 23° C. The mixture was cooled to −78° C. and reacted with 0.53 ml of trifluoromethanesulfonic anhydride in 0.50 ml of dichloromethane to form alpha-anomer enriched 2-deoxy-2,2-difluoro-D-ribofuranosyl-3,5-dibenzoate-1-trifluoromethanesulfate in solution. Care was taken to maintain the temperature of the reaction mixture below −65° C.

A 1.85 g suspension of 2,6-dipivalamidopurine was prepared in 30 ml of acetonitrile and maintained anhydrous under a nitrogen atmosphere. 651 mg of potassium t-butoxide were added to the suspension and the resulting mixture stirred at 23° C. for 15 minutes to form a 2,6-dipivalamidopurine potassium salt. The salt suspension was added to 20 ml of dry dichloromethane, cooled to 0° C. and reacted with the alpha-anomer enriched 2-deoxy-2,2-difluoro-D-ribofuranosyl-3,5-dibenzoyl-1-trifluoromethanesulfonate solution, stirred for 1 hour and warmed to 23° C. to form the titled blocked nucleoside which was confirmed by HPLC analysis. The beta to alpha anomeric ratio of the blocked nucleoside was 2:1.

To extract the nucleoside product from the reaction mixture, 50 ml of ethyl acetate and 50 ml of 1N hydrochloric acid were added. The organic layer was separated and washed with 50 ml of 5% sodium bicarbonate. The organic layer was separated and washed with 50 ml of saturated aqueous sodium chloride and dried over magnesium sulfate.

EXAMPLE 3

Preparation of beta-anomer enriched 9-[1-(2'-deoxy-2',2'-difluoro-3',5'-di-O-benzoyl-D-ribofuranosyl)]-6-chloropurine with 2 equivalents of 6-chloropurine potassium salt To 1.4 g of 2-deoxy-2,2-difluoro-D-ribofuranosyl-3,5-dibenzoate were added 14 ml of dichloromethane and 0.515 ml of triethylamine. This solution was stirred at 23° C. for 15 minutes, cooled to −40° C. and reacted with 0.621 ml of trifluoromethanesulfonic anhydride to form alpha-anomer enriched 2-deoxy-2,2-difluoro-D-ribofuranosyl-3,5-dibenzoyl-1-trifluoromethanesulfonate in solution.

A 155 mg suspension of 6-chloropurine was prepared in 3 ml of acetonitrile and maintained anhydrous under a nitrogen atmosphere. 130 mg of potassium t-butoxide were added to the suspension and the resulting mixture was stirred at 23° C. for 10 minutes to form a 6-chloropurine potassium salt. The salt suspension was cooled to 0° C. and reacted with 2 ml of the alpha-anomer enriched 2-deoxy-2,2-difluoro-D-ribofuranosyl-3,5-dibenzoyl-1-trifluoromethanesulfonate solution, stirred for 1 hour and warmed to 22° C. to form the titled blocked nucleoside which was confirmed by HPLC analysis. The beta to alpha anomeric ratio of the blocked nucleoside was 2:1.

To extract the nucleoside product from the reaction mixture, 25 ml of ethyl acetate, 1 ml of water, 1 ml of 1N hydrochloric acid and 2 ml of a saturated aqueous sodium chloride solution were added. The organic layer was separated, washed with 5 ml of saturated aqueous sodium bicarbonate solution and 5 ml of brine and dried over magnesium sulfate. A quantitative HPLC analysis revealed a yield of blocked beta-anomer nucleoside of 27 percent.

EXAMPLE 4

Preparation of beta-anomer enriched 9-[1-(2'-deoxy-2',2'-difluoro-3',5'-di-O-benzoyl-D-ribofuranosyl)]-2,6-dichloro-3-deazapurine with 2 equivalents of 2,6-dichloro-3-deazapurine potassium salt To 1.4 g of 2-deoxy-2,2-difluoro-D-ribofuranosyl-3,5-dibenzoate were added 14 ml of dichloromethane and 0.515 ml of triethylamine. This solution was stirred at 23° C. for 15 minutes, cooled to −40° C. and reacted with 0.621 ml of trifluoromethanesulfonic anhydride to form alpha-anomer enriched 2-deoxy-2,2-difluoro-D-ribofuranosyl-3,5-dibenzoyl-1-trifluoromethanesulfonate in solution.

A 82 mg suspension of 2,6-dichloro-3-deazapurine was prepared in 1.5 ml of acetonitrile and maintained anhydrous under a nitrogen atmosphere. 49 mg of potassium t-butoxide were added to the suspension and the resulting mixture was stirred at 23° C. for 10 minutes to form a 2,6-dichloro-3-deazapurine potassium salt. The salt suspension was cooled to 0° C. and reacted with the alpha-anomer enriched 2-deoxy-2,2-difluoro-D-ribofuranosyl-3,5-dibenzoyl-1-trifluoromethanesulfonate solution, stirred for 1 hour and warmed to 20° C. to form the titled blocked nucleoside which was confirmed by HPLC analysis. The beta to alpha anomeric ratio of the blocked nucleoside was 2.5:1.

To extract the nucleoside product from the reaction mixture, 25 ml of ethyl acetate, 1 ml of water, 1 ml of 1N hydrochloric acid and 2 ml of a saturated aqueous sodium chloride solution were added. The organic layer was separated, washed with 5 ml of saturated aqueous sodium bicarbonate solution and 5 ml of brine and dried over magnesium sulfate. A quantitative HPLC analysis revealed a combined yield of blocked beta-anomer nucleoside of 21 percent, mp 127° C.–129° C.

EXAMPLE 5

Preparation of beta-anomer enriched 9-[1-(2'-deoxy-2',2'-difluoro-3',5'-di-O-benzoyl-D-ribofuranosyl)]-2,6-dichloropurine with 2 equivalent of 2,6-dichloropurine potassium salt To 1.4 g of 2-deoxy-2,2-difluoro-D-ribofuranosyl-3,5-dibenzoate were added 14 ml of dichloromethane and 0.515 ml of triethylamine. This solution was stirred at 23° C. for 15 minutes then cooled to −40° C. and reacted with 0.621 ml of trifluoromethanesulfonic anhydride to form alpha-anomer enriched 2-deoxy-2,2-difluoro-D-ribofuranosyl-3,5-dibenzoyl-1-trifluoromethanesulfonate in solution.

A 220 mg suspension of 2,6-dichloropurine was prepared in 3 ml of acetonitrile and maintained anhydrous under a nitrogen atmosphere. 130 mg of potassium t-butoxide were added and the resulting mixture was stirred at 23° C. for 10 minutes to form a 2,6-dichloropurine potassium salt. The salt suspension was cooled to 0° C. and reacted with the alpha-anomer enriched 2-deoxy-2,2-difluoro-D-ribofuranosyl-3,5-dibenzoyl-1 -trifluoromethanesulfonate solution, stirred for 1 hour and warmed to 22° C. to form the titled blocked nucleoside which was confirmed by HPLC analysis. The beta to alpha anomeric ratio of the blocked nucleoside was 2.5:1.

To extract the nucleoside product from the reaction mixture, 25 ml of ethyl acetate, 1 ml of water, 1 ml of 1N hydrochloric acid and 2 ml of a saturated aqueous sodium chloride solution were added. The organic layer was separated, washed with 5 ml of saturated aqueous sodium bicarbonate solution, 5 ml of brine and dried over magnesium sulfate. A quantitative HPLC analysis revealed a yield of blocked beta-anomer nucleoside of 22 percent.

EXAMPLE 6

Preparation of beta-anomer enriched 1-[1-(2'-deoxy-2',2'-difluoro-3',5'-di-O-benzoyl-D-ribofuranosyl)]-3-carboethoxy-1,2,4-triazole with 2 equivalents of 3-carboethoxy-1,2,4-triazole potassium salt To 1.4 g of 2-deoxy-2,2-difluoro-D-ribofuranosyl-3,5-dibenzoate were added 14 ml of dichloromethane and 0.515 ml of triethylamine. This solution was stirred at 23° C. for 15 minutes, cooled to −40° C. and reacted with 0.621 ml of trifluoromethanesulfonic anhydride to form alpha-anomer enriched 2-deoxy-2,2-difluoro-D-ribofuranosyl-3,5-dibenzoyl-1-trifluoromethanesulfonate in solution.

A 164 mg suspension of triazole ester was prepared in 3 ml of acetonitrile and maintained anhydrous under a nitrogen atmosphere. 131 mg of potassium t-butoxide were added and the resulting mixture was stirred at 23° C. for 10 minutes to form a 3-carboethoxy-1,2,4-triazole potassium salt. The salt suspension was cooled to 0° C. and reacted with 2 ml of the alpha-anomer enriched 2-deoxy-2,2-difluoro-D-ribofuranosyl-3,5-dibenzoyl-1-trifluoromethanesulfonate solution, stirred for 40 minutes and warmed to 15° C. to form the titled blocked nucleoside which was confirmed by HPLC analysis. The beta to alpha anomeric ratio of the blocked nucleoside was 2.5:1.

To extract the nucleoside product from the reaction mixture, 25 ml of ethyl acetate, 1 ml of water, 1 ml of 1N hydrochloric acid and 2 ml of a saturated aqueous sodium chloride solution were added. The organic layer was separated, washed with 5 ml of saturated aqueous sodium bicarbonate solution, 5 ml of brine and dried over magnesium sulfate. A quantitative HPLC analysis revealed a yield of blocked beta-anomer nucleoside of 14 percent.

EXAMPLE 7

Preparation of beta-anomer enriched 9-[1-(2'-deoxy-2',2'-difluoro-3',5'-di-O-benzoyl-D-ribofuranosyl)]-2-amino-6-chloropurine with 2 equivalents of 2-amino-6-chloropurine potassium salt To 1.4 g of 2-deoxy-2,2-difluoro-D-ribofuranosyl-3,5-dibenzoate were added 14 ml of dichloromethane and 0.515 ml of triethylamine. This solution was stirred at 23° C. for 15 minutes, cooled to −40° C. and reacted with 0.621 ml of trifluoromethanesulfonic anhydride to form alpha-anomer enriched 2-deoxy-2,2-difluoro-D-ribofuranosyl-3,5-dibenzoyl-1-trifluoromethanesulfonate in solution.

A 197 mg suspension of 2-amino-6-chloropurine was prepared in 3 ml of acetonitrile and maintained anhydrous under a nitrogen atmosphere. 130 mg of potassium t-butoxide were added and the resulting mixture was stirred at 23° C. for 10 minutes to form a 2-amino-6-chloropurine potassium salt. The salt suspension was cooled to 0° C. and reacted with 2 ml of the alpha-anomer enriched 2-deoxy-2,2-difluoro-D-ribofuranosyl-3,5-dibenzoyl-1-trifluoromethanesulfonate solution, stirred for 1 hour and warmed to 22° C. to form the titled blocked nucleoside which was confirmed by HPLC analyses. The beta to alpha anomeric ratio of the blocked nucleoside was 2:1.

To extract the nucleoside product from the reaction mixture, 100 ml of ethyl acetate, 10 ml of water were added and a precipitate formed. The precipitate was filtered off, washed with 5 ml of saturated aqueous sodium bicarbonate solution, 5 ml of brine and dried over magnesium sulfate. A quantitative HPLC analysis revealed a yield of blocked beta-anomer nucleoside of 14 percent.

EXAMPLE 8

Preparation of beta-anomer enriched 9-[1-(2'-deoxy-2',2'-difluoro-3',5'-di-O-benzoyl-D-ribofuranosyl)]-2,6-dipivalamidopurine with 2 equivalents of 2,6-dipivalamidopurine potassium salt To 3.78 g of 2-deoxy-2,2-difluoro-D-ribofuranosyl-3,5-dibenzoate were added 30 ml of dichloromethane and 1.39 ml of triethylamine. This solution was stirred at 23° C. for 15 minutes, cooled to −40° C. and reacted with 1.68 ml of trifluoromethanesulfonic anhydride to form alpha-anomer enriched 2-deoxy-2,2-difluoro-D-ribofuranosyl-3,5-dibenzoyl-1-trifluoromethanesulfonate in solution.

A 6.99 g suspension of 2,6-dipivalamidopurine was prepared in 100 ml of acetonitrile and maintained anhydrous under a nitrogen atmosphere. 2.46 g of potassium t-butoxide were added and the resulting mixture was stirred at 23° C. for 10 minutes and dried to constant weight in vacuo at 40° C. to form a 2,6-dipivalamidopurine potassium salt. The salt suspension was added to 100 ml dichloromethane, cooled to 0° C. and reacted with the alpha-anomer enriched 2-deoxy-2,2-difluoro-D-ribofuranosyl-3,5-dibenzoyl-1-trifluoromethanesulfonate solution, stirred for 1 hour and warmed to 22° C. to form the titled blocked nucleoside which was confirmed by HPLC analysis.

To extract the nucleoside product from the reaction mixture, 500 ml of ethyl acetate, 20 ml of ice, 20 ml of 1N hydrochloric acid and 35 ml of a saturated aqueous sodium chloride solution were added. The organic layer was separated, washed with 25 ml of saturated aqueous sodium bicarbonate solution, 25 ml of brine and dried over magnesium sulfate. The beta to alpha anomeric ratio of the blocked nucleoside was 1.8:1. A quantitative HPLC analysis revealed a yield of blocked beta-anomer nucleoside of 28 percent, mp 238° C.–239° C.

EXAMPLE 9

Preparation of beta-anomer enriched 9-[1-(2'-deoxy-2',2'-difluoro-3',5'-di-O-benzoyl-D-ribofuranosyl)]-6-pivalamidopurine with 2 equivalents of 6-pivalamidopurine potassium salt To 1.4 g of 2-deoxy-2,2-difluoro-D-ribofuranosyl-3,5-dibenzoate were added 14 ml of dichloromethane and 0.515 ml of triethylamine. This solution was stirred at 23° C. for 15 minutes, cooled to −40° C. and reacted with 0.621 ml of trifluoromethanesulfonic anhydride to form alpha-anomer enriched 2-deoxy-2,2-difluoro-D-ribofuranosyl-3,5-dibenzoyl-1-trifluoromethanesulfonate in solution.

A 255 mg suspension of 6-pivalamidopurine was prepared in 3 ml of acetonitrile and maintained anhydrous under a nitrogen atmosphere. 131 mg of potassium t-butoxide were added and the resulting mixture was stirred at 23° C. for 10 minutes to form a 6-pivalamidopurine potassium salt. The salt suspension was cooled to 0° C. and reacted with the alpha-anomer enriched 2-deoxy-2,2-difluoro-D-ribofuranosyl-3,5-dibenzoyl-1-trifluoromethanesulfonate solution, stirred for 1 hour and warmed to 22° C. to form the titled blocked nucleoside which was confirmed by HPLC analysis. The beta to alpha anomeric ratio of the blocked nucleoside was 2:1.

To extract the nucleoside product from the reaction mixture, 25 ml of ethyl acetate, 1 ml of water, 1 ml of 1N hydrochloric acid and 2 ml of a saturated aqueous sodium chloride solution were added. The organic layer was separated, washed with 5 ml of saturated aqueous sodium bicarbonate solution, 5 ml of brine and dried over magnesium sulfate. A quantitative HPLC analysis revealed a combined yield of blocked beta- and alpha-anomer nucleoside of 28 percent.

EXAMPLE 10

Preparation of beta-anomer enriched 9-[1-(2'-deoxy-2',2'-difluoro-3',5'-di-O-benzoyl-D-ribofuranosyl)]-8-bromo-7-cyano-7-deaza-6-pivalamidopurine with 2 equivalents of 8-bromo-7-cyano-7-deaza-6-pivalamidopurine potassium salt To 1.4 g of 2-deoxy-2,2-difluoro-D-ribofuranosyl-3,5-dibenzoate were added 14 ml of dichloromethane and 0.515 ml of triethylamine. This solution was stirred at 23° C. for 15 minutes, cooled to −40° C. and reacted with 0.621 ml of trifluoromethanesulfonic anhydride to form alpha-anomer enriched 2-deoxy-2,2-difluoro-D-ribofuranosyl-3,5-dibenzoyl-1-trifluoromethanesulfonate in solution.

A suspension of 187 mg of 8-bromo-7-cyano-7-deaza-6-pivalamidopurine was prepared in 3 ml of acetonitrile and maintained anhydrous under a nitrogen atmosphere. 65 mg of potassium t-butoxide were added and the resulting mixture was stirred at 23° C. for 10 minutes to form a 8-bromo-7-cyano-7-deaza-6-pivalamidopurine potassium salt. The salt suspension was cooled to 0° C. and reacted with 1 ml of the alpha-anomer enriched 2-deoxy-2,2-difluoro-D-ribofuranosyl-3,5-dibenzoyl-1-trifluoromethanesulfonate solution, stirred for 1 hour and warmed to 20° C. to formed the titled blocked nucleoside which was confirmed by HPLC analysis. The beta to alpha anomeric ratio of the blocked nucleoside was 2:1.

To extract the nucleoside product from the reaction mixture, 25 ml of ethyl acetate, 1 ml of water, 1 ml of 1N hydrochloric acid and 2 ml of a saturated aqueous sodium chloride solution were added. The organic layer was separated, washed with 5 ml of saturated aqueous sodium bicarbonate solution, 5 ml of brine and dried over magnesium sulfate. A quantitative HPLC analysis revealed a combined yield of blocked beta- and alpha-anomer nucleoside of 24 percent.

EXAMPLE 11

Preparation of beta-anomer enriched 9-[1-(2'-deoxy-2',2'-difluoro-3',5'-di-O-benzoyl-D-ribofuranosyl)]-2,6-dipivalamidopurine with 2 equivalents of 2,6-dipivalamidopurine potassium salt in various reaction solvents To 1 g of 2-deoxy-2,2-difluoro-D-ribofuranosyl-3,5-dibenzoate was added 10 ml of dichloromethane and 0.36 ml of triethylamine. This solution was stirred at 23° C. for 15 minutes, cooled to −40° C. and reacted with 0.45 ml of trifluoromethanesulfonic anhydride to form alpha-anomer enriched 2-deoxy-2,2-difluoro-D-ribofuranosyl-3,5-dibenzoyl-1-trifluoromethanesulfonate in solution.

A 1.85 g suspension of 2,6-dipivalamidopurine was prepared in 30 ml of acetonitrile and maintained anhydrous under a nitrogen atmosphere. 0.65 g of potassium t-butoxide were added and the resulting mixture was stirred at 25° C. for 10 minutes to form a 2,6-dipivalamidopurine potassium salt. The salt suspension was dried in vacuo at 40° C. to form a white solid of constant weight. 207 mg of the purine salt was suspended in 1.5 ml of the solvent shown in Runs A–F in the table below, under nitrogen at 0° C. and reacted with 1 ml of the alpha-anomer enriched 2-deoxy-2,2-difluoro-D-ribofuranosyl-3,5-dibenzoyl-1-trifluoromethanesulfonate solution, stirred for 1 hour and warmed to 0° C. to form the titled blocked nucleoside which was confirmed by HPLC analysis. The beta to alpha anomeric ratios of the blocked nucleoside is shown below.

To extract the nucleoside product from the reaction mixture, 25 ml of ethyl acetate, 1 ml of water, 1 ml of 1N hydrochloric acid and 2 ml of a saturated aqueous sodium chloride solution were added. The organic layer was separated, washed with 2 ml of saturated aqueous sodium bicarbonate solution, 5 ml of brine and dried over magnesium sulfate. A quantitative HPLC analysis revealed a yield of blocked beta-anomer nucleoside shown below:

| Run | Solvent | β/α Nucleoside Ratio | β Yield (%) |
|---|---|---|---|
| A | Tetrahydrofuran | 1.3:1 | 45 |
| B | Toluene | 1.8:1 | 49 |
| C | Ethylacetate | 1.6:1 | 47 |
| D | Dichloroethane | 2.1:1 | 55 |
| E | t-Butylalcohol | 3.5:1 | 53 |
| F | Acetonitrile | 1.6:1 | 40 |

EXAMPLE 12

Preparation of beta-anomer enriched 9-[1-(2'-deoxy-2',2'-difluoro-3',5'-di-O-benzoyl-D-ribofuranosyl)]-2-acetamido-6-diphenylcarbamoyloxypurine with 2 equivalents of 2-acetamido-6-diphenylcarbamoyloxy purine potassium salt To 1.4 g of 2-deoxy-2,2-difluoro-D-ribofuranosyl-3,5-dibenzoate were added 14 ml of dichloromethane and 0.515 ml of triethylamine. This solution was stirred at 23° C. for 15 minutes, cooled to −40° C. and reacted with 0.621 ml of trifluoromethanesulfonic anhydride to form alpha-anomer enriched 2,2-difluoro-2-deoxy-D-ribofuranosyl-3,5-dibenzoyl-1-trifluoromethanesulfonate in solution.

A solution of 2.56 g 2-acetamido-6-diphenylcarbamoyloxypurine was prepared in 50 ml of hot dimethylformamide and maintained anhydrous under a nitrogen atmosphere. The solution was cooled to 25° C. and 0.74 g of potassium t-butoxide were added. The resulting mixture was stirred at 23° C. for 10 minutes and evaporated to an oil which was triturated with ether, collected on a filter, and dried in vacuo at 40° C. to form a 2-acetamido-6-diphenyl carbamoyloxy purine potassium salt. 496 mg of the purine salt were suspended in 3 ml dichloromethane, cooled to 5° C. and reacted with the alpha-anomer enriched 2-deoxy-2,2-difluoro-D-ribofuranosyl-3,5-dibenzoyl-1-trifluoromethanesulfonate solution, stirred for 1 hour and warmed to 25° C. to form the titled blocked nucleoside which was confirmed by HPLC analysis. The beta to alpha anomeric ratio of the blocked nucleoside was 1.8:1.

To extract the nucleoside product from the reaction mixture, 25 ml of ethyl acetate, 1 ml of water, 1 ml of 1N hydrochloric acid and 2 ml of a saturated aqueous sodium chloride solution were added. The organic layer was separated, washed with 5 ml of saturated aqueous sodium bicarbonate solution, 5 ml of brine and dried over magnesium sulfate. The yield of blocked beta-anomer nucleoside was 5.8 percent.

EXAMPLE 13

Preparation of beta-anomer enriched 9-[1-(2'-deoxy-2',2'-difluoro-3',5'-di-O-benzoyl-D-ribofuranosyl)]-2,6-dipivalamidopurine with 7 equivalents of 2,6-dipivalamidopurine potassium salt To 100 mg of 2-deoxy-2,2-difluoro-D-ribofuranosyl-3,5-dibenzoate were added 3 ml of dichloromethane and 0.036 ml of triethylamine. This solution was stirred at 23° C. for 15 minutes, cooled to −78° C. and reacted with 0.045 ml of trifluoromethanesulfonic anhydride to form alpha-anomer enriched 2-deoxy-2,2-difluoro-D-ribofuranosyl-3,5-dibenzoyl-1-trifluoromethanesulfonate in solution.

A 1.85 g suspension of 2,6-dipivalamidopurine was prepared in 30 ml of acetonitrile and maintained anhydrous under a nitrogen atmosphere. 0.65 g of potassium t-butoxide were added and the resulting mixture was stirred at 23° C. for 10 minutes and dried in vacuo at 40° C. to form a 2,6-dipivalamidopurine potassium salt which was cooled to −78° C. The purine salt were reacted with the alpha-anomer enriched 2-deoxy-2,2-difluoro-D-ribofuranosyl-3,5-dibenzoyl-1-trifluoromethanesulfonate solution at 23° C., stirred for 1.5 hours and warmed to 22° C. to form the titled blocked nucleoside which was confirmed by HPLC analysis.

To extract the nucleoside product from the reaction mixture, 25 ml of ethyl acetate, 1 ml of ice, 1 ml of 1N hydrochloric acid and 2 ml of a saturated aqueous sodium chloride solution were added. The organic layer was separated, washed with 5 ml of saturated aqueous sodium bicarbonate solution, 5 ml of brine and dried over magnesium sulfate. The beta to alpha anomeric ratio of the blocked nucleoside was 2.7:1.

The present invention has been described in detail, including the preferred embodiments thereof. However, it will be appreciated that those skilled in the art, upon consideration of the present disclosure, may make modifications and/or improvements on this invention that fall within the scope and spirit of the invention as set forth in the following claims.

What is claimed is:

1. A stereoselective glycosylation process for preparing a beta-anomer enriched nucleoside of the formula

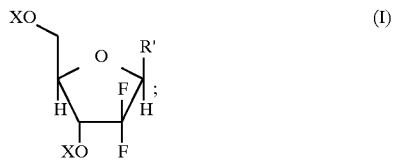

wherein each X is independently selected from hydroxy protecting groups and R' is a nucleobase selected from the group consisting of

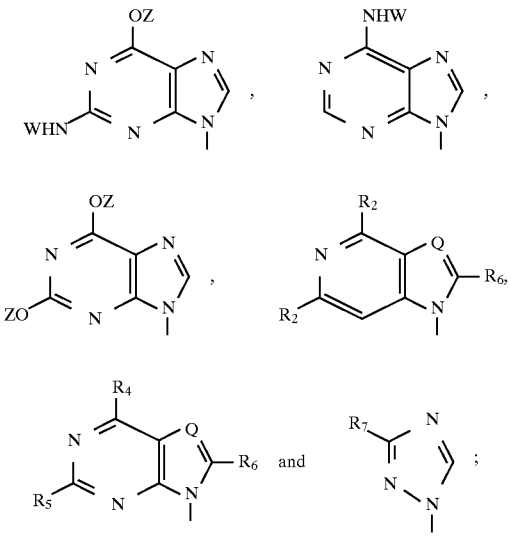

wherein $R_2$ is halo; $R_4$, $R_5$ and $R_6$ are independently selected from the group consisting of hydrogen, —OZ, —NHW, —N(alkyl)W, halo, alkoxy and thioalkyl; $R_7$ is selected from the group consisting of hydrogen, halo, cyano, alkyl, alkoxy, alkoxycarbonyl, thioalkyl, thiocarboxamido and carboxamido; Q is selected from the group consisting of CH, $CR_8$ and N; wherein $R_8$ is selected from the group consisting of halo, carboxamido, thiocarboxamido, alkoxycarbonyl and cyano; Z is a hydroxy protecting group and W is an amino protecting group; comprising reacting an alpha-anomer enriched 2,2-difluorocarbohydrate of the formula

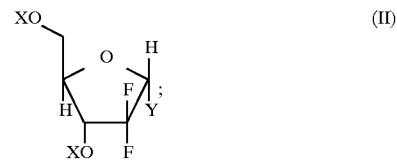

wherein Y is selected from the group consisting of trifluoromethanesulfonyloxy, 1,1,1-trifluoroethanesulfonyloxy, octafluorobutanesulfonyloxy and nonafluorobutanesulfonyloxy and each X is as defined above; with at least 2 molar equivalents of a nucleobase derivative, R″, selected from the group consisting of

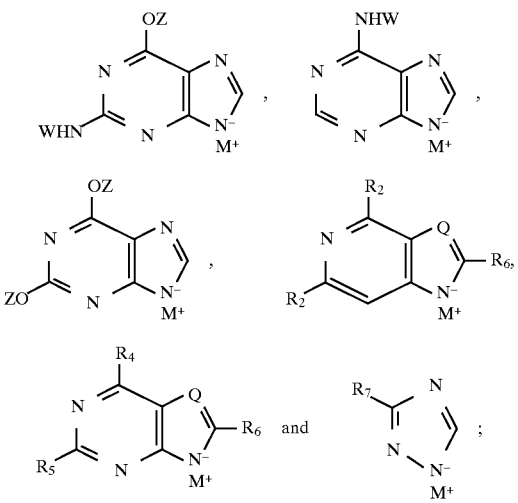

wherein $R_2$ through $R_7$, Q, Z and W are as defined above and $M^+$ is a metal cation; at temperatures from about −120° C. to about 25° C. in a low freezing inert solvent.

2. The process of claim 1 wherein the amount of R″ is from between greater than 2 molar equivalents and about 20 molar equivalents.

3. The process of claim 1 wherein $M^+$ is a lithium, sodium or a potassium metal cation.

4. The process of claim 1 wherein Z and W are selected from the group consisting of carboxamidos, carboethoxy, carbamoyloxy, acetamido and acetyl.

5. The process of claim 4 wherein Z and W are pivaloyl.

6. The process of claim 1 wherein X is selected from the group consisting of mono-substituted benzoyl, disubstituted benzoyl and benzoyl.

7. The process of claim 1 wherein Y is trifluoromethanesulfonyloxy and the reaction temperature is from about −50° C. to about 10° C.

8. The process of claim 1 wherein Y is 1,1,1-trifluoroethanesulfonyloxy, octafluorobutanesulfonyloxy or nonafluorobutanesulfonyloxy and the reaction temperature is from about −20° C. to about 25° C.

9. The process of claim 1 further comprising deblocking to form a beta-anomer enriched nucleoside of the formula

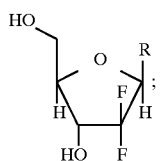

wherein R is a deblocked nucleobase selected from the group consisting of

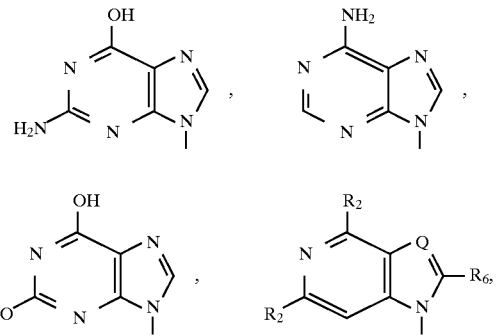

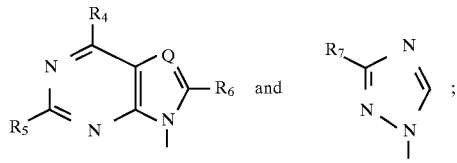

wherein $R_2$ is halo; $R_4$, $R_5$ and $R_6$ are independently selected from the group consisting of hydrogen, —OH, —$NH_2$, —N(alkyl)W, halo, alkoxy and thioalkyl; $R_7$ is selected from the group consisting of hydrogen, halo, cyano, alkyl, alkoxy, alkoxycarbonyl, thioalkyl, thiocarboxamido and carboxamido; Q is selected from the group consisting of CH, $CR_8$ and N; wherein $R_8$ is selected from the group consisting of halo, carboxamido, thiocarboxamido, alkoxycarbonyl and cyano.

\* \* \* \* \*